United States Patent [19]

Immel et al.

[11] Patent Number: 4,514,578
[45] Date of Patent: Apr. 30, 1985

[54] PROCESS FOR THE PREPARATION OF TRIMETHYLOLPROPANE

[75] Inventors: Otto Immel; Hans-Helmut Schwarz; Hein Quast; Eberhard Bandtel, all of Krefeld, Fed. Rep. of Germany

[73] Assignee: Bayer Aktiengesellschaft, Leverkusen, Fed. Rep. of Germany

[21] Appl. No.: 623,279

[22] Filed: Jun. 22, 1984

Related U.S. Application Data

[63] Continuation of Ser. No. 466,693, Feb. 15, 1983, abandoned.

[30] Foreign Application Priority Data

Mar. 4, 1982 [DE] Fed. Rep. of Germany ....... 3207746

[51] Int. Cl.³ .................... C07C 31/22; C07C 29/38
[52] U.S. Cl. .................................................. 568/853
[58] Field of Search ........................................ 568/853

[56] References Cited

U.S. PATENT DOCUMENTS

| | | | |
|---|---|---|---|
| 2,135,063 | 11/1938 | Walker et al. | 568/853 |
| 2,170,624 | 8/1939 | Wyler | 568/853 |
| 2,534,191 | 12/1950 | Gryer et al. | 568/853 |
| 2,775,622 | 12/1956 | Snow | 568/853 |
| 3,076,854 | 2/1963 | Klein | 568/853 |
| 3,504,042 | 3/1970 | Shimono et al. | 568/853 |
| 4,122,290 | 10/1978 | Immel et al. | 568/853 |

FOREIGN PATENT DOCUMENTS

| | | | |
|---|---|---|---|
| 2431814 | 1/1975 | Fed. Rep. of Germany | 568/853 |
| 134514 | 3/1979 | German Democratic Rep. | 568/858 |
| 34965 | 11/1969 | Japan | 568/853 |
| 904780 | 8/1962 | United Kingdom | 568/853 |
| 1163428 | 9/1969 | United Kingdom | 568/853 |

Primary Examiner—J. E. Evans
Attorney, Agent, or Firm—Sprung, Horn, Kramer & Woods

[57] ABSTRACT

Trimethylolpropane is prepared in such a manner that butyraldehyde is metered into a mixture of water, alkaline condensing agent and formaldehyde, which contains less than 0.1 mol of methanol relative to 1 mol of formaldehyde, at temperatures from 15° to 50° C., and after addition of the butyraldehyde the reaction mixture is heated up to 90° C., sufficient water being present in the reaction mixture so that the reaction mixture has a content of trimethylolpropane of 5 to 25% by weight after the reaction.

18 Claims, No Drawings

PROCESS FOR THE PREPARATION OF TRIMETHYLOLPROPANE

This is a continuation of application Ser. No. 466,693 filed Feb. 15, 1983, now abandoned.

The invention relates to a process for the preparation of trimethylolpropane by reaction of n-butyraldehyde with aqueous formaldehyde in the presence of alkaline condensing agents.

It has been disclosed, in German Auslegeschrift No. 1,153,739, German Auslegeschrift No. 1,154,080, German Auslegeschrift No. 1,182,646 and U.S. Pat. No. 3,076,854 that trimethylolpropane is prepared by alkaline condensation of formaldehyde with butyraldehyde. The disadvantages of these processes are the yields, which are unsatisfactory for a large-scale process, and the high industrial costs necessary in some cases (several reaction steps, for example, in the process of German Auslegeschrift No. 1,154,080 and German Auslegeschrift No. 1,153,739).

Furthermore, a process has been disclosed in German Democratic Republic Pat. No. 134,514 in which trimethylolpropane is prepared by alkaline condensation of approximately stoichiometric amounts of n-butyraldehyde and aqueous formaldehyde in the presence of a mixture of calcium hydroxide and sodium hydroxide as the condensing agent and by setting up a minimum content of water in the reaction mixture. The disadvantage of this process is that the calcium formate, which is produced as an important by-product is contaminated with sodium formate, it being possible to remove the sodium formate only at relatively high industrial cost. In addition, on repeating the process described in the German Democratic Republic patent specification, the high yields of trimethylolpropane reported there could not be achieved (compare the Comparison Example to Example 2 of the process according to the invention).

Another possibility of preparing trimethylolpropane consists of initially reacting butyraldehyde with formaldehyde under alkaline reaction conditions to give dimethylolbutanal and then catalytically hydrogenating the latter to give trimethylolpropane (compare, for example, German No. 2,702,582 and U.S. Pat. No. 4,122,290). It is true that satisfactory yields of trimethylolpropane are achieved with this process (up to 94.5% of theory according to the German patent, but it is less suitable for a large-scale process, since the catalytic hydrogenation must be carried out in a high pressure apparatus, which necessitates additional industrial costs.

A process for the preparation of trimethylolpropane by the reaction of n-butyraldehyde with aqueous formaldehyde in the presence of alkaline condensing agents has now been found, which is characterized in that the butyraldehyde is metered into a mixture of water, alkaline condensing agent and formaldehyde, which contains less than 0.1 mol of methanol relative to 1 mol of formaldehyde, at temperatures from 15° to 50° C., and after addition of the butyraldehyde the reaction mixture is heated up to 90° C., sufficient water being present in the reaction mixture so that the reaction mixture has a content of trimethylolpropane of 5 to 25% by weight after the reaction.

In general, in the process according to the invention, the formaldehyde is employed in the form of an aqueous solution having a content of about 10 to 40% by weight of formaldehyde, preferably having a content of 20 to 30% by weight of formaldehyde. The formaldehyde employed for this process should contain less than 0.1 mol of methanol, preferably 0 to 0.07 mol of methanol, particularly preferably 0.001 to 0.05 mol of methanol, relative to 1 mol of formaldehyde.

Suitable alkaline condensing agents are those bases known and customarily used for the aldol condensation. Examples which may be mentioned are the hydroxides and/or carbonates of alkali metals and/or alkaline earth metals such as sodium hydroxide, potassium hydroxide, calcium hydroxide, barium hydroxide and/or sodium carbonate, preferably sodium hydroxide and/or calcium hydroxide, particularly preferably calcium hydroxide.

In general, in the process according to the invention, the alkaline condensing agents are employed in an amount of about 0.5 to 1.7 mols per mol of n-butyraldehyde. When using alkali metal hydroxides, customarily about 1 to 1.7, preferably 1.2 to 1.6, mols of alkali metal hydroxide is used per mol of butyraldehyde and, when employing alkaline earth metal hydroxides, about 0.5 to 1, preferably 0.6 to 0.8 mol of alkaline earth metal hydroxide is employed per mol of butyraldehyde.

In general, in the process according to the invention, 1 mol of butyraldehyde is reacted with about 3.0 to 10, preferably 3.1 to 8, particularly preferably 3.2 to 7, mols of formaldehyde.

Care should be taken in the reaction according to the invention that sufficient water is present in the reaction mixture so that the reaction mixture has a content of trimethylolpropane of about 5 to 25, preferably 6 to 17, particularly preferably 7 to 10, % by weight after the reaction. The necessary water content in the reaction mixture can be set up in this process by an appropriate excess of aqueous formaldehyde or by the addition of water.

The process according to the invention is customarily carried out at temperatures from about 15° to 90° C., the start of the reaction initially being carried out at low temperatures, at about 15° to 50° C., preferably at 20° to 40° C., and then the reaction mixture is heated to higher temperatures, say 90° C., preferably 50° to 80° C., to complete the reaction. The temperature range in which the reaction is carried out most advantageously depends, inter alia, on the pH of the reaction mixture and can easily be found by preliminary experiments. For example, when the pH of the reaction mixture is about 11, the reaction is initially carried out at 20° to 30° C. and the mixture is then heated to 40° to 50° C.

The reaction times necessary for the process according to the invention are very dependent on the reaction temperature and are generally about 5 minutes to 2 hours.

The process according to the invention can be carried out advantageously by initially introducing the aqueous formaldehyde, the desired alkaline condensing agent and, if desired water and metering in the n-butyraldehyde at temperatures from 15° to 50° C. However, one can also initially introduce only a part of the formaldehyde and add the remaining formaldehyde together with the butyraldehyde. In this instance, the butyraldehyde is advantageously added at the rate at which it is consumed to the initially introduced mixture. After addition of the butyraldehyde, the reaction mixture is heated to about 80° C. to complete the reaction.

After completion of the reaction, the pH of the reaction mixture, which is about 7 to 10, depending on the base employed in each case and the amount of formaldehyde employed, is adjusted to a value in the range from about 5 to 7, preferably 5.5 to 6.5, by the addition of acids, such as formic, acetic, sulphuric and/or phosphoric acid. If an excess of formaldehyde is present in the reaction mixture, the formaldehyde can be distilled out at temperatures of about 120° to 150° C. and under a pressure of about 2 to 5 bar, and thus be recovered in this manner.

The working up of the reaction mixture can be carried out in a customary manner by distillation or extraction (compare, for example, Ullmanns Enzyklopädie der technischen Chemie (Ullmann's Encyclopaedia of Industrial Chemistry) 4th edition, volume 7, page 231 (1974)).

The process according to the invention can be carried out both continuously and also discontinuously.

The advantage of the process according to the invention lies in the high yields of trimethylolpropane, relative to the butyraldehyde employed or the formaldehyde employed or reacted. Thus, the process can be carried out particularly economically on a large industrial scale. Furthermore, fewer by-products are formed in the process according to the invention than in the known processes, and thus the working up of the reaction mixture and the purification of the trimethylolpropane is considerably simplified.

However, it is particularly surprising that the yields of trimethylolpropane, relative to the formaldehyde employed or reacted, in the process according to the invention could be increased further, and this means that the economics of the process can be regarded as being extremely favourable in respect of the consumption of formaldehyde.

Trimethylolpropane is an intermediate of industrial importance for the preparation of plasticisers, raw materials for paints, polyesters and polyurethanes (compare, for example, Ullmanns Enzyklopädie der technischen Chemie (Ullmann's Encyclopaedia of Industrial Chemistry) 4th edition, volume 7, page 228 and page 231 (1974)).

The following examples are intended to elucidate the process according to the invention but without restricting it to these examples.

EXAMPLE 1

4,800 g (32 mols) of a 20% strength aqueous formaldehyde solution having a methanol content of 0.43% (0.64 mol) are initially introduced into a 6 l stirred flask and 176 g (4.4 mols) of sodium hydroxide, dissolved in 704 g of water, are added. The solution is maintained at 30° C., while 300 g (4.04 mols) of n-butyraldehyde (97% pure) are metered in regularly within 1 hour. Subsequently, the reaction mixture is heated to 48° C. and maintained at this temperature for 1 hour. The reaction product (5,980 g) thus obtained contains 8.56% of trimethylolpropane (3.82 mols) and 9.7% of formaldehyde (19.3 mols). The yield of trimethylolpropane is 94.5% relative to n-butyraldehyde employed and 90.3% relative to reacted formaldehyde. The unreacted formaldehyde is recovered in a customary manner by distillation under pressure.

Comparison Example to Example 1 (carried out according to Example 1 of German Auslegeschrift No. 1,182,646)

20% strength aqueous formaldehyde in an amount of 4,800 g (32 mols) having a commercial methanol content of 4.1% (corresponding to 6.1 mols) are placed in a stirred flask of volume 6 l and 176 g (4.4 mols) of sodium hydroxide, dissolved in 700 g of water, are added. 296 g (3.98 mols) of n-butyraldehyde (97% pure) are metered in regularly to this solution, at an initial temperature of 28° C., with stirring in the course of 1 hour. Due to the reaction taking place exothermically, the temperature rises to 49° C. After addition of the n-butyraldehyde the reaction product is heated to 57° C. and maintained at this temperature for 1 hour. The reaction product (5,972 g) is analyzed as in Example 1. It contains 7.95% of trimethylolpropane (3.54 mols) and 9.6% of formaldehyde (19.1 mols). The yield of trimethylolpropane is 88.9% relative to the n-butyraldehyde employed and 82.3% relative to the reacted formaldehyde.

EXAMPLE 2

200 g of calcium hydroxide are added to 4,400 g of an aqueous formalin solution, which contains 3.4% of formaldehyde (5 mols) and 0.08% of methanol (0.1 mol), and the mixture is stirred. 800 g of formalin, which contains 30% of formaldehyde (8 mols) and 0.7% of methanol (0.2 mol) are pumped regularly into this mixture at 30° C. within 1 hour. Simultaneously, and also in the course of 1 hour, 300 g of 97% pure n-butyraldehyde (4.036 mols) are metered in. During this, the mixture is stirred vigorously and the temperature is maintained at 30° C. The reaction mixture (5,700 g) is then heated to 60° C. The reaction product thus obtained contains 8.62% of trimethylolpropane (3.66 mols), corresponding to a yield of 90.7% of trimethylolpropane, relative to the butyraldehyde employed and 84.5% of theory, relative to the formaldehyde employed.

Comparison Example to Example 2 (carried out according to Example 2 of German Democratic Republic Patent Specification No. 134,514)

2,454 g (12.3 mols) of a 15% strength aqueous formaldehyde solution, having a commercial methanol content of 3.1% (2.4 mols), were initially introduced, at 20° C., into a stirred flask of volume 6 l. In the course of 80 minutes, 299 g (4.02 mols) of butyraldehyde (97% pure) and 1,830 g (1.1 mols) of a 1.8% strength aqueous formaldehyde solution were pumped in regularly and 146 g (1.97 mols) of calcium hydroxide powder and 40.9 ml of a 20% strength sodium hydroxide solution (0.2 mol) were metered in. During this, the reaction temperature was limited to a maximum of 40° C. The reaction mixture obtained after completion of the main reaction was maintained at 65° C. for 45 minutes. The reaction product (4,762 g) thus obtained contained 9.94% of trimethylolpropane (3.53 mols) corresponding to a yield of trimethylolpropane of 88.3%, relative to the n-butyraldehyde employed and 79% relative to the formaldehyde employed.

EXAMPLE 3

5,200 g of 18.5% strength aqueous formaldehyde solution (32 mols), which contained 0.4% of methanol (0.65 mol), were initially introduced into a stirred flask of volume 6 l at 25° C. and 200 g of calcium hydroxide powder (2.7 mols) were added. In the course of 1 hour, with vigorous stirring, 300 g of (97% pure) n-butyraldehyde (4.036 mols) were metered in regularly, the reaction temperature being maintained at 25° C. by cooling. After addition of the butyraldehyde, the reaction mixture was heated to 45° C. and maintained at this temperature for 1 hour. The reaction product was analysed. It contained 8.86% of trimethylolpropane and 10.1% of formaldehyde, corresponding to a yield of trimethylolpropane of 93.4% relative to the butyraldehyde employed, and a yield of 88.3% relative to the reacted formaldehyde.

What is claimed is:

1. In a process for the preparation of trimethylolpropane by reaction of n-butyraldehyde with aqueous formaldehyde in the presence of an alkaline condensing agent, the improvement wherein the n-butyraldehyde is metered into a reaction mixture of water, alkaline condensing agent and formaldehyde, which contains less than 0.1 mol of methanol per mol of formaldehyde, at a temperature from 15° to 50° C. and, after addition of said butyraldehyde, the reaction mixture's temperature is increased to a temperature up to 90° C., the process being carried out in the presence of sufficient water such that the reaction mixture has a content of trimethylolpropane of 5 to 10% by weight after the reaction.

2. A process according to claim 1, wherein the initial reaction of n-butyraldehyde with formaldehyde is carried out at a temperature of between 20° and 40° C. and thereafter, following the addition of the butyraldehyde, the temperature of the reaction mixture is adjusted so as to be in the range of 50° to 90° C.

3. A process according to claim 1, wherein the initial reaction of n-butyraldehyde with formaldehyde is carried out at a temperature of between 20° and 40° C. and thereafter, following the addition of the butyraldehyde, the temperature of the reaction mixture is adjusted so as to be in the range of 50° to 80° C.

4. A process according to claim 1, wherein the water content of the reaction mixture is established by employing an appropriate excess of aqueous formaldehyde.

5. A process according to claim 1, wherein the water content of the reaction mixture is established by adding water thereto.

6. A process according to claim 1, wherein the formaldehyde employed contains 0 to 0.07 mol of methanol per mol of formaldehyde.

7. A process according to claim 6, wherein said formaldehyde contains 0.001 to 0.05 mol of methanol per mol of formaldehyde.

8. A process according to claim 1, wherein said alkaline condensing agent is present in an amount of 0.5 to 1.7 mols per mol of n-butyraldehyde.

9. A process according to claim 1, wherein said alkaline condensing agent is sodium hydroxide.

10. A process according to claim 1, wherein said alkaline condensing agent is calcium hydroxide.

11. A process according to claim 10, wherein said calcium hydroxide is substantially free of sodium hydroxide.

12. A process according to claim 1, wherein said formaldehyde is employed in an amount of 3 to 10 mols per mol of n-butyraldehyde.

13. A process according to claim 1, wherein sufficient water is present in the reaction mixture such that after the reaction the reaction mixture has a trimethylolpropane content of 6 to 10% by weight.

14. A process according to claim 1, wherein the process is carried out employing a reaction mixture whose pH is about 11 and the process is carried out initially at a temperature of 20° to 30° C. and is thereafter heated to a temperature in the range of 40° to 50° C.

15. A process according to claim 1, wherein the process is carried out between 5 minutes and 2 hours.

16. A process according to claim 1, wherein after completion of the reaction, the pH of the reaction mixture is about 7 to 10 and the pH is adjusted to a value in the range from about 5 to 7 by the addition of an acid.

17. A process according to claim 16, wherein said acid is selected from the group consisting of formic acid, acetic acid, sulfuric acid, and phosphoric acid.

18. A process according to claim 1, wherein the process is carried out in the presence of sufficient water such that the reaction mixture has a content of trimethylolpropane of 7 to 10% by weight after the reaction.

* * * * *